United States Patent [19]
Yoo et al.

[11] Patent Number: 5,691,348
[45] Date of Patent: Nov. 25, 1997

[54] PYRIDYL IMIDAZOLE DERIVATIVES AND PROCESSES FOR THE PREPARATION THEREOF

[75] Inventors: Sung-Eun Yoo; Kyu-Yang Yi; Sang-Hee Lee; Hye-Ryung Kim; Jee-Hee Suh; Nak-Jeong Kim; Seon-Ju Kim; Ok-Ja Cha; Young-Ah Shin; Wha-Sup Shin; Sung-Hou Lee; Yi-Sook Jung; Byung-Ho Lee; Ho-Won Seo; Hye-Suk Lee, all of Daejeon, Rep. of Korea

[73] Assignee: Daewoo Electronics Co., Ltd., Seoul, Rep. of Korea

[21] Appl. No.: 750,460

[22] PCT Filed: Jun. 7, 1995

[86] PCT No.: PCT/KR95/00075

§ 371 Date: Dec. 6, 1996

§ 102(e) Date: Dec. 6, 1996

[87] PCT Pub. No.: WO95/34564

PCT Pub. Date: Dec. 21, 1995

[30]  Foreign Application Priority Data

Jun. 11, 1994 [KR] Rep. of Korea ............... 94-13163
May 8, 1995 [KR] Rep. of Korea ............... 95-11100

[51] Int. Cl.[6] ................. A61K 31/435; C07D 471/04
[52] U.S. Cl. .......................... 514/300; 546/118
[58] Field of Search ........................ 546/118; 514/303

[56]  References Cited

U.S. PATENT DOCUMENTS 5,332,744  7/1994  Chakravarty et al. ............... 546/118

*Primary Examiner*—Bernard Dentz
*Attorney, Agent, or Firm*—Anderson Kill & Olick, P.C.

[57]  ABSTRACT

Novel pyridyl imidazole derivatives of formula(I) inhibit effectively the action of angiotensin II and have a superior antihypertensive activity:

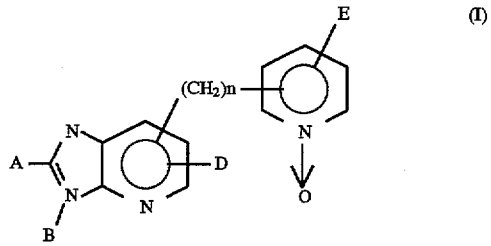

wherein:

A is a straight, branched or cyclic $C_1$–$C_6$ alkyl or alkenyl group, $OR^1$ (wherein $R^1$ is a hydrogen, or a straight, branched or cyclic $C_1$–$C_6$ alkyl or alkenyl radical), or $NR^2R^3$ (wherein $R^2$ and $R^3$ are independently a hydrogen, or a straight, branched or cyclic $C_1$–$C_6$ alkyl radical);

B is a group of the following formula

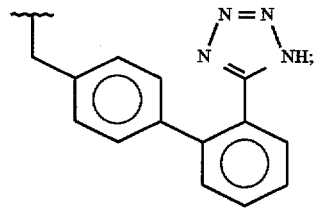

D is a hydrogen; a halogen; a straight, branched or cyclic $C_1$–$C_6$ alkyl, $C_2$–$C_6$ alkenyl or $C_2$–$C_6$ alkynyl group which is optionally substituted with OH, a $C_1$–$C_4$ alkoxy radical, $CO_2R^1$, $COR^1$, $CON(R^1)_2$ or $N(R^1)_2$, wherein $R^1$ is the same as defined above; tetrazol-5-yl; a perfluoro-$C_1$–$C_4$ alkyl group; or $N(R^1)_2$, $OR^1$, $CO_2R^1$ or $CON(R^1)_2$, wherein $R^1$ is the same as defined above;

E is a hydrogen; a halogen; a straight or branched $C_1$–$C_6$ alkyl, $C_2$–$C_6$ alkenyl or $C_2$–$C_6$ alkynyl group which is optionally substituted with OH, a $C_1$–$C_4$ alkoxy radical, $CO_2R^1$, $COR^1$, $CON(R^1)_2$ or $N(R^1)_2$, wherein $R^1$ is the same as defined above; a perfluoro-$C_1$–$C_4$ alkyl group; $NO_2$; or $N(R^1)_2$ or $OR^1$, wherein $R^1$ is the same as defined above; and n is 0 or an integer of 1 to 4.

9 Claims, 2 Drawing Sheets

PYRIDYL IMIDAZOLE DERIVATIVES AND PROCESSES FOR THE PREPARATION THEREOF

This application is a 371 of PCT/KR/00075 filed Jun. 7, 1995.

FIELD OF THE INVENTION

The present invention relates to novel pyridyl imidazole derivatives substituted with N-oxide, processes for preparing them and pharmaceutical compositions containing same as active ingredients.

DESCRIPTION OF THE PRIOR ART

Various imidazole derivatives, which can inhibit the action of angiotensin II, have been used for the treatment of hypertension caused by angiotensin II. Angiotensin II is produced by an angiotensin converting enzyme from angiotensin I, which is formed from angiotensinogen by the action of renin. Angiotensin II, which is a potent vaso-constrictor interacting with specific receptors on cell membrane, has been reported to cause hypertension in mammals including human beings.

Many studies have been made to search for an antagonist which inhibits the action of angiotensin II on the receptors of its target cell in order to suppress the elevation of blood pressure. As a result, many imidazole derivatives have been developed (see A. T. Chiu et al., *Eur. J. Pharm.*, 157, 13(1981); P. C. Wong et al., *J. Pharmacol. Exp. Ther.*, 247, 1(1988); and, P. C. Wong et al., *Hypertension*, 13, 489(1989)).

As a representative of these compounds, for example, D. J. Carini et al. reported in *J. Med. Chem.*, 34, 2525(1990) imidazole derivatives of the following formula(A):

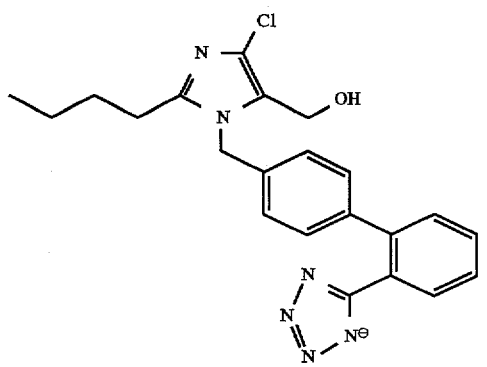

Further, EP No. 400,974 discloses imidazole derivatives of the following formula(B):

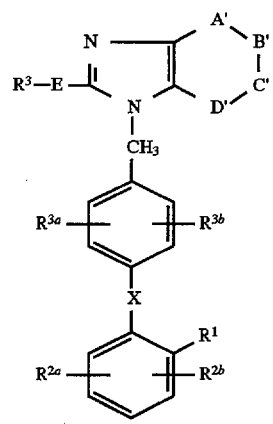

wherein:

—A'—B'—C'—D'— represents the constituent atoms of a 6-membered heterocycle having 1 to 3 nitrogen atoms such as —C($R^7$)=C($R^7$)—C($R^7$)=N— wherein each of $R^7$'s is independently a hydrogen atom, or a substituted alkyl or aryl group or heterocycle (e.g., —C(CH$_3$)=CH—C(CH$_3$)=N—).

Despite these discoveries, however, needs have continued to exist for the development of more effective agents which possess enhanced antagonistic properties against angiotensin II.

SUMMARY OF THE INVENTION

Accordingly, it is an object of the present invention to provide novel pyridyl imidazole derivatives of formula(I) and pharmacologically acceptable salts thereof, having an enhanced ability to suppress the activity of angiotensin II:

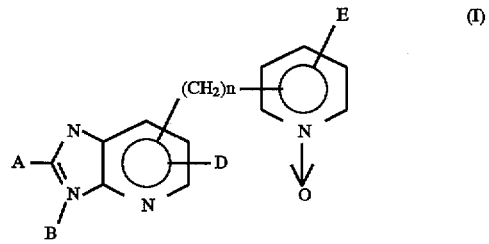

wherein:

A is a straight, branched or cyclic $C_1$–$C_6$ alkyl or alkenyl group, OR$^1$ (wherein R$^1$ is a hydrogen, or a straight, branched or cyclic $C_1$–$C_6$ alkyl or alkenyl radical), or NR$^2$R$^3$ (wherein R$^2$ and R$^3$ are independently a hydrogen, or a straight, branched or cyclic $C_1$–$C_6$ alkyl radical);

B is a group of the following formula

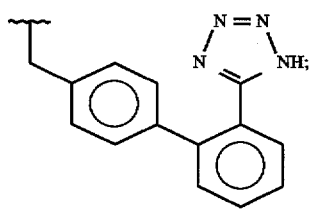

D is a hydrogen; a halogen; a straight, branched or cyclic $C_1$–$C_6$ alkyl, $C_2$–$C_6$ alkenyl or $C_2$–$C_6$ alkynyl group which is optionally substituted with OH, a $C_1$–$C_4$ alkoxy radical, CO₂R¹, COR¹, CON(R¹)₂ or N(R¹)₂, wherein R¹ is the same as defined above; tetrazol-5-yl; a perfluoro-$C_1$-$C_4$ alkyl group; or N(R¹)₂, OR¹, CO₂R¹ or CON(R¹)₂, wherein R¹ is the same as defined above;

E is a hydrogen; a halogen; a straight or branched $C_1$-$C_6$ alkyl, $C_2$-$C_6$ alkenyl or $C_2$-$C_6$ alkynyl group which is optionally substituted with OH, a $C_1$-$C_4$ alkoxy radical, CO₂R¹, COR¹, CON(R¹)₂ or N(R¹)₂, wherein R¹ is the same as defined above; a perfluoro-$C_1$-$C_4$ alkyl group; NO₂; or N(R¹)₂ or OR¹, wherein R¹ is the same as defined above; and n is 0 or an integer of 1 to 4.

Another object of the present invention is to provide processes for preparing the inventive derivatives, and to provide pharmaceutical compositions containing same as active ingredients.

DETAILED DESCRIPTION OF THE INVENTION

Figure 1A:
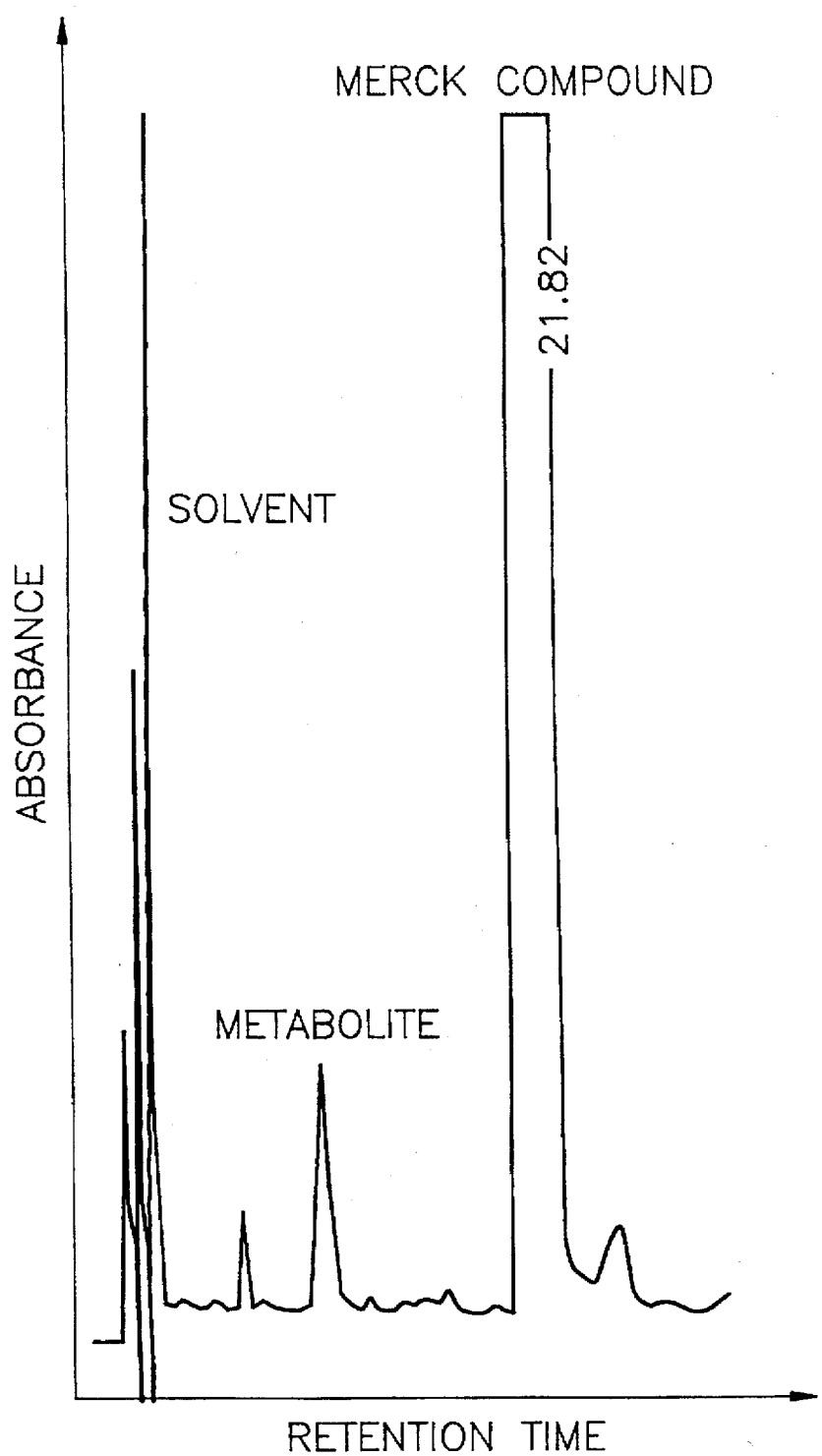
FIG. 1 is a HPLC chart showing the result of the enzyme digestion test of a reference "Merck" compound (FIG. 1A) and a compound prepared in Example 3 (FIG. 1B), respectively.

Among the compounds of formula(I), preferred are those wherein:

A is a straight, branched or cyclic $C_2$-$C_6$ alkyl group or OR¹ (wherein R¹ is a straight, branched or cyclic $C_2$-$C_5$ alkyl radical);

B is a group of the following formula

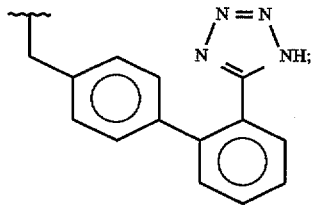

D is a hydrogen, a straight, branched or cyclic $C_1$-$C_4$ alkyl or alkenyl group which is optionally substituted with OH, a $C_1$-$C_2$ alkoxy radical, CO₂R¹, COR¹ or N(R¹)₂, wherein R¹ is the same as defined above;

E is a hydrogen, or a straight, branched or cyclic $C_1$-$C_4$ alkyl or alkenyl group; and n is 0, 1 or 2.

Exemplary compounds of formula(I) of the present invention are as follows:

2-butyl-5-methyl-6-(1-oxy-pyridin-2-yl)-3-[2'-(1H-tetrazol-5-yl)-biphenyl-4-ylmethyl]-3H-imidazo[4,5-b]pyridine;
2-butyl-5-methyl-6-(1-oxy-2-methyl-pyridin-6-yl)-3-[2'-(1H-tetrazol-5-yl)-biphenyl-4-ylmethyl]-3H-imidazo[4,5-b]pyridine;
2-butyl-5-methyl-6-(1-oxy-3-methyl-pyridin-6-yl)-3-[2'-(1H-tetrazol-5-yl)-biphenyl-4-ylmethyl]-3H-imidazo[4,5-b]pyridine;
2-butyl-5-methyl-6-(1-oxy-4-methyl-pyridin-6-yl)-3-[2'-(1H-tetrazol-5-yl)-biphenyl-4-ylmethyl]-3H-imidazo[4,5-b]pyridine;
2-butyl-5-methyl-6-(1-oxy-pyridin-3-yl)-3-[2'-(1H-tetrazol-5-yl)-biphenyl-4-ylmethyl]-3H-imidazo[4,5-b]pyridine;
2-butyl-5-methyl-6-(1-oxy-pyridin-4-yl)-3-[2'-(1H-tetrazol-5-yl)-biphenyl-4-ylmethyl]-3H-imidazo[4,5-b]pyridine;
2-butyl-5-methyl-6-(1-oxy-2-methyl-pyridin-3-yl)-3-[2'-(1H-tetrazol-5-yl)-biphenyl-4-ylmethyl]-3H-imidazo[4,5-b]pyridine;
2-butyl-5-methyl-6-(1-oxy-6-methyl-pyridin-3-yl)-3-[2'-(1H-tetrazol-5-yl)-biphenyl-4-ylmethyl]-3H-imidazo[4,5-b]pyridine;
2-butyl-5-hydroxymethyl-6-(1-oxy-pyridin-2-yl)-3-[2'-(1H-tetrazol-5-yl)-biphenyl-4-ylmethyl]-3H-imidazo[4,5-b]pyridine;
2-butyl-5-(2-hydroxyethyl-1-yl)-6-(1-oxy-pyridin-2-yl)3-[2'-(1H-tetrazol-5-yl)-biphenyl-4-ylmethyl]-3H-imidazo[4,5-b]pyridine;
2-butyl-5-methoxycarbonyl-6-(1-oxy-pyridin-2-yl)-3-[2'-(1H-tetrazol-5-yl)-biphenyl-4-ylmethyl]-3H-imidazo[4,5-b]pyridine;
2-butyl-5-(N,N-diethylcarbamoyl)-6-(1-oxy-pyridin-2-yl)-3-[2'-(1H-tetrazol-5-yl)-biphenyl-4-ylmethyl]-3H-imidazo[4,5-b]pyridine;
2-butyl-6-(1-oxy-pyridin-2-yl)-3-[2'-(1H-tetrazol-5-yl)biphenyl-4-ylmethyl]-3H-imidazo[4,5-b]pyridine;
2-butyl-5-(N,N-dimethylamino)-6-(1-oxy-pyridin-2-yl)-3-[2'-(1H-tetrazol-5-yl)-biphenyl-4-ylmethyl]-3H-imidazo[4,5-b]pyridine;
2-butyl-5-ethyl-6-(1-oxy-pyridin-2-yl)-3-[2'-(1H-tetrazol-5-yl)-biphenyl-4-ylmethyl]-3H-imidazo[4,5-b]pyridine;
2-butyl-5-fluoro-6-(1-oxy-pyridin-2-yl)-3-[2'-(1H-tetrazol-5-yl)-biphenyl-4-ylmethyl]-3H-imidazo[4,5-b]pyridine;
2-butyl-5-methyl-6-(1-oxy-pyridin-2-ylmethyl)-3-[2'-(1H-tetrazol-5-yl)-biphenyl-4-ylmethyl]-3H-imidazo[4,5-b]pyridine;
2-butyl-5-methyl-6-(1-oxy-pyridin-3-ylmethyl)-3-[2'-(1H-tetrazol-5-yl)-biphenyl-4-ylmethyl]-3H-imidazo[4,5-b]pyridine;
2-butyl-5-methyl-6-[2-(1-oxy-pyridin-2-yl)ethyl-1-yl]-3-[2'-(1H-tetrazol-5-yl)-biphenyl-4-ylmethyl]-3H-imidazo[4,5-b]pyridine;
2-butyl-5-methyl-6-[2-(1-oxy-pyridin-3-yl)ethyl-1-yl]-3-[2'-(1H-tetrazol-5-yl)-biphenyl-4-ylmethyl]-3H-imidazo[4,5-b]pyridine;
2-ethyl-5-methyl-6-(1-oxy-pyridin-2-yl)-3-[2'-(1H-tetrazol-5-yl)-biphenyl-4-ylmethyl]-3H-imidazo[4,5-b]pyridine;
2-ethoxy-5-methyl-6-(1-oxy-pyridin-2-yl)-3-[2'-(1H-tetrazol-5-yl)-biphenyl-4-ylmethyl]-3H-imidazo[4,5-b]pyridine;
2-propyl-5-methyl-6-(1-oxy-pyridin-2-yl)-3-[2'-(1H-tetrazol-5-yl)-biphenyl-4-ylmethyl]-3H-imidazo[4,5-b]pyridine;
2-butyl-5-hydroxymethyl-6-(1-oxy-2-methyl-pyridin-6-yl)-3-[2'-(1H-tetrazol-5-yl)-biphenyl-4-ylmethyl]-3H-imidazo[4,5-b]pyridine;
2-butyl-5-hydroxymethyl-6-(1-oxy-pyridin-4-yl)-3-[2'-(1H-tetrazol- 5-yl)-biphenyl-4-ylmethyl]-3H-imidazo[4,5-b]pyridine; and
2-butyl-5-hyroxymethyl-6-(1-oxy-pyridin-3-yl)-3-[2'-(1H-tetrazol-5-yl)-biphenyl-4-ylmethyl]-3H-imidazo[4,5-b]pyridine.

Preferred compounds of formula (I) of the present invention are as follows:

2-butyl-5-methyl-6-(1-oxy-pyridin-2-yl)-3-[2'-(1H-tetrazol-5-yl)-biphenyl-4-ylmethyl]-3H-imidazo[4,5-b]pyridine;
2-butyl-5-methyl-6-(1-oxy-2-methyl-pyridin-6-yl)-3-[2'-(1H-tetrazol-5-yl)-biphenyl-4-ylmethyl]-3H-imidazo[4,5-b]pyridine;
2-butyl-5-methyl-6-(1-oxy-pyridin-3-yl)-3-[2'-(1H-tetrazol-5-yl)-biphenyl-4-ylmethyl]-3H-imidazo[4,5-b]pyridine;
2-butyl-5-methyl-6-(1-oxy-pyridin-4-yl)-3-[2'-(1H-tetrazol-5-yl)-biphenyl-4-ylmethyl]-3H-imidazo[4,5-b]pyridine;
2-butyl-5-hydroxymethyl-6-(1-oxy-pyridin-2-yl)-3-[2'-(1H-tetrazol-5-yl)-biphenyl-4-ylmethyl]-3H-imidazo[4,5-b]pyridine;

2-butyl-5-methoxycarbonyl-6-(1-oxy-pyridin-2-yl)-3-[2'-(1H-tetrazol-5-yl)-biphenyl-4-ylmethyl]-3H-imidazo[4,5-b]pyridine;

2-butyl-6-(1-oxy-pyridin-2-yl)-3-[2'-(1H-tetrazol-5-yl)-biphenyl-4-ylmethyl]-3H-imidazo[4,5-b]pyridine;

2-butyl-5-hydroxymethyl-6-(1-oxy-2-methyl-pyridin-6-yl)-3-[2'-(1H-tetrazol-5-yl)-biphenyl-4-ylmethyl]-3H-imidazo[4,5-b]pyridine;

2-butyl-5-hyroxymethyl-6-(1-oxy-pyridin-4-yl)-3-[2'-(1H-tetrazol-5-yl)-biphenyl-4-ylmethyl]-3H-imidazo[4,5-b]pyridine; and 2-butyl-5-hyroxymethyl-6-(1-oxy-pyridin-3-yl)-3-[2'-(1H-tetrazol- 5-yl)-biphenyl-4-ylmethyl]-3H-imidazo[4,5-b]pyridine.

The pyridyl imidazole derivatives substituted with N-oxide of formula(I) of the present invention may be prepared as described below.

Diamino pyridine compound of formula(II) is condensed with a carboxylic acid of formula ACOOH or an ester of formula ACOOR, wherein A is the same as defined previously and R is a methyl or ethyl group, to produce a pyridyl imidazole derivative of formula(III):

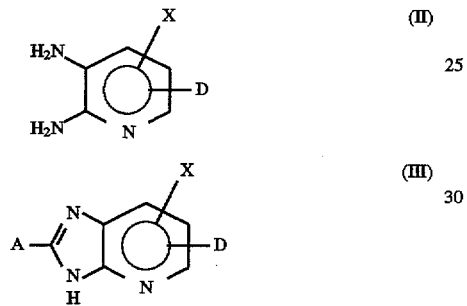

wherein:

X is a halogen such as Br or I, or trifluoromethanesulfonate; and

A and D are the same as defined in formula(I) above.

The pyridyl imidazole derivative of formula(III) is reacted with a compound of formula(IV) in the presence of a base to give a pyridyl imidazole derivative of formula(V):

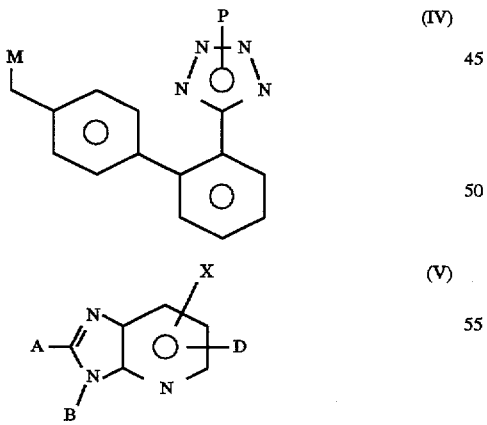

wherein:

M is a leaving group;

P is a tetrazole protecting group; and

A, B, D and X are the same as defined in formula(I), (II) or (III) above.

The leaving group may be a halogen such as Cl or Br, tosylate or methanesulfonate, and the tetrazole protecting group may be triphenylmethyl or 1-ethoxyethyl. Representative examples of the base are sodium hydride, sodium alkoxide and calcium carbonate. The reaction may be carried out in a solvent such as dimethyl formamide, dimethyl sulfoxide, acetone or alcohol at a temperature ranging from 0° C. to a boiling point of the solvent.

The compound of formula(V) is reacted with the compound of formula(VI) in the presence of tetrakis (triphenylphosphine) palladium(0) to give a pyridine compound of formula(VIII). The compound of formula(VIII) is hydrogenated in the presence of a palladium catalyst to give a pyridine compound of formula(VII).

Alternatively, the compound of formula(VIII) is oxidized with ozone to give an aldehyde compound of formula(IX); the compound(IX) is then reacted with the compound of formula(X) to produce an alcohol compound of formula (XI); the compound(XI) is reacted with methanesulfonyl chloride to give a compound of formula(XII); and, then, the resulting compound(XII) is reduced with tributyltin hydride to produce a pyridine compound of formula(VII):

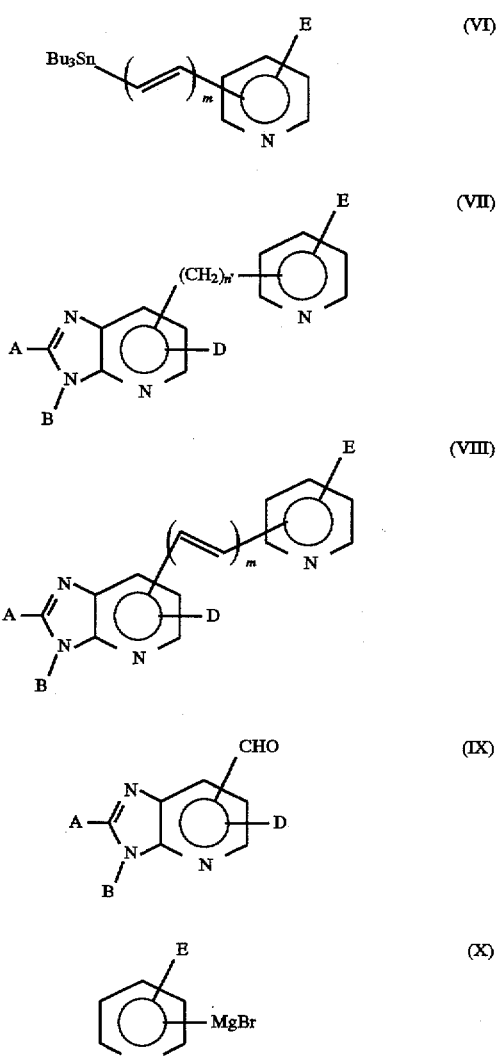

-continued

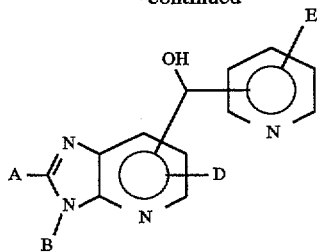
(XI)

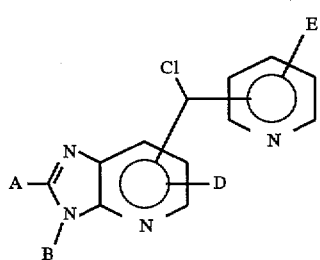
(XII)

wherein:

A, B, D and E are the same as defined in formula(I) above;

m is 0 or 1; and n' is 0 or 2.

Finally, the compound of formula(VII) is oxidized with an oxidizing agent to give the compound of formula(I).

Representative examples of the oxidizing agent are m-chloroperbenzoic acid, oxone, hydrogen peroxide-acetic acid and hydrogen peroxide-trifluoroacetic acid.

The following compounds of formula(XV) and formula (XVII) which are intermediates for preparing a compound of formula(V) wherein D is substituted on the 5-position thereof may be prepared as described below.

The compound of formula(XIII) is oxidized with the above oxidizing agent to give a N-oxide compound of formula(XIV). Thereafter, the compound(XIV) is heated to reflux in the presence of acetic anhydride to give an ester of the compound of formula(XV), which is hydrolyzed with a base to give a compound of formula(XV):

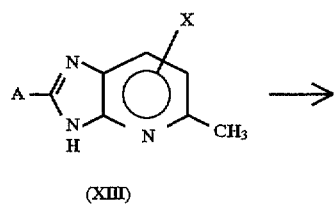
(XIII)

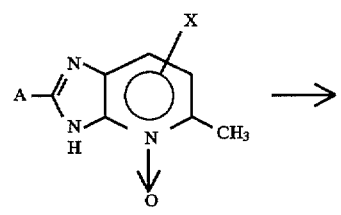
(XIV)

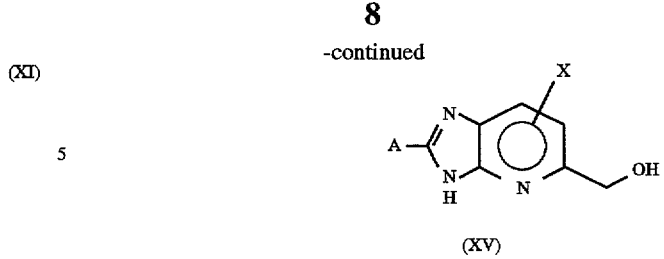
(XV)

wherein A and X are the same as defined in formula(I), (II) or (III) above.

The compound of formula(XV) is further oxidized with an oxidizing agent to give an aldehyde compound of formula (XVI). The oxidizing agent may be a conventional one such as manganese dioxide, dimethylsulfoxide-oxalyl chloride, chromium trioxide, etc.

The aldehyde compound of formula(XVI) is reacted with bromine or NaHCO$_3$ in the presence of a solvent such as methanol to give a methyl ester, which is then transesterified to give an alkyl ester of formula(XVII):

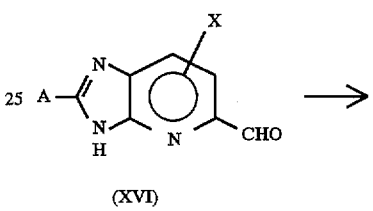
(XVI)

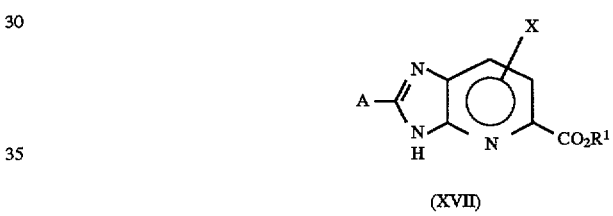
(XVII)

wherein A, R$^1$ and X are the same as defined in formula(I) or (II) above.

The present invention also provides pharmacologically acceptable salts, preferably, sodium or potassium salts of the compounds of formula(I) which may be prepared by a conventional method.

The novel pyridyl imidazole derivatives of the present invention and pharmacologically acceptable salts thereof have an antihypertensive activity due to the antagonistic action against angiotensin II; and, therefore, may be useful for the treatment of acute or chronic cardiac deficiencies and various renal disorders as well as hypertension. The compounds of the present invention may be also useful for the treatment of migraine, Raynaud's disease and various ocular diseases caused by elevated intraocular pressure and for the retardation of progress of atherosclerosis.

The compounds may be used alone or together with other antihypertensive agents such as a diuretic, an angiotensin converting enzyme inhibitor, a calcium-channel blocker, a potassium-channel blocker and the like.

Accordingly, the present invention also provides pharmaceutical compositions containing the compounds of formula (I) and pharmaceutically acceptable salts thereof as active ingredients and pharmacologically acceptable carriers.

The pharmaceutical compositions of the present invention may be administered orally or parenterally. These compositions may be in a unit dosage form of tablets, capsules or powder. The pharmaceutical composition in a unit dosage may comprise about 0.1 to 1000 mg, preferably 1 to 500 mg of the active ingredient; and may be administered 4 times or less, preferably once or twice per day for an adult depending on the age and body weight of the patient, the kind and severity of the illness, and so on. The compositions of the present invention may comprise conventional adjuvants such as filler, binder, lubricant and flavoring agent. The formulation may be carried out in accordance with a conventional method.

The following Examples are intended to illustrate the present invention more specifically, without limiting the scope of the invention. The percentages as used in the Examples are by v/v, unless otherwise specified.

EXAMPLE 1

Preparation of 2-Butyl-5-hydroxymethyl-6-(1-oxy-pyridin-2-yl)-3-[2'-(1H-tetrazol-5-yl)-biphenyl-4-ylmethyl]-3H-imidazo[4,5-b]pyridine Step 1: Preparation of 6-amino-5-bromo-picoline 32.4 g (0.3 mole) of 6-aminopicoline was dissolved in a mixture of 28 g of conc. sulfuric acid and 120 ml of water and the resulting solution was cooled in ice water. 52.8 g (0.33 mole) of bromine was added dropwise to the solution over 30 minutes at 0° C. The reaction solution was stirred for 20 minutes at room temperature and neutralized with cold aqueous NaOH solution. The resultant was filtered and the solid was purified with column chromatography using methylene chloride and ethyl acetate as an eluent to obtain 31 g of the title compound (yield 55%).

Step 2: Preparation of 3-bromo-5-nitro-6-amino-2-picoline 20 g (0.107 mole) of the compound obtained in step 1 was dissolved in 110 ml of conc. sulfuric acid and thereto was added dropwise 9.4 ml (0.12 mole) of nitric acid for 30 minutes at 0° C. The reaction solution was stirred for 1 hour at 0° C. and, subsequently stirred for another 1 hour at room temperature. The resultant was neutralized with cold 40% aqueous NaOH solution and filtered to get a yellow solid. The solid was washed with distilled water (100 ml×3) and dried in a vacuum oven at 60° C. for 24 hours to obtain 23.8 g of the title compound (yield 96%).

Step 3: Preparation of 3-bromo-5,6-diamino-2-picoline 7.7 g (33.2 mmole) of the compound obtained in step 2 was dissolved in a mixture of 27 ml of ethanol and 7 ml of water and to the resulting solution were added 20 g (0.36 mole) of iron powder and 0.33 ml of conc. hydrochloric acid. The resultant was refluxed with stirring for 1 hour, filtered through Cellite to remove the remaining iron powder and washed with ethanol (50 ml×3). The filtrate was concentrated under reduced pressure and the residue was dissolved in ethyl acetate. The resultant was passed through silica gel and concentrated under reduced pressure to obtain 6.6 g of the title compound (yield 98%).

Step 4: Preparation of 6-bromo-2-butyl-5-methyl-1H-imidazo[4,5-b]pyridine 9.0 g (44.6 mmole) of the compound obtained in step 3 and 5.5 g (58 mmole) of valeric acid were mixed with 30 ml of polyphosphoric acid and stirred for 3 hours at 110° C. The reaction solution was dissolved in a mixture of 50 ml of cold water and 50 ml of THF and the resulting solution was neutralized to Ph 8 with cold 40% aqueous NaOH solution with stirring vigorously and extracted with ethyl acetate (50 ml×3). Thereafter, the organic layer was dried over $Na_2SO_4$, concentrated under reduced pressure and recrystallized from hexane-methylene chloride to obtain 9.8 g of the title compound (yield 82%).

Step 5: Preparation of 6-bromo-2-butyl-5-methyl-1H-imidazo[4,5-b]pyridine-4-oxide 7.8 g (29.1 mmole) of the compound obtained in step 4 was dissolved in 50 ml of methylene chloride and to the resulting solution was added 8.8 g (43.6 mmole) of 85% m-chloroperbenzoic acid. The resultant was stirred for 16 hours at room temperature and filtered to get a solid, which was washed with ethyl ether (12 ml×3) to obtain 8.0 g of the title compound (yield 97%).

Step 6: Preparation of 6-bromo-2-butyl-5-hydroxymethyl-1H-imidazo[4,5-b]pyridine 8.0 g (28.17 mmole) of the compound obtained in step 5 was dissolved in 20 ml of anhydrous acetic acid. The resulting solution was stirred for 1 hour at 120° C., and evaporated under reduced pressure to remove anhydrous acetic acid. Thereafter, the residue was dissolved in a mixture of 30 ml of methanol and 40 ml of 3N LiOH. The resulting solution was refluxed for 1 hour, evaporated under reduced pressure to remove methanol, neutralized with 1N HCl and extracted with ethyl acetate (50 ml×3). The organic layer was dried over $Na_2SO_4$, concentrated under reduced pressure and purified with column chromatography (hexane:ethyl acetate=1:2) to obtain 5.3 g of the title compound (yield 66%).

Step 7: Preparation of 6-bromo-2-butyl-5-formyl-1H-imidazo[4,5-b]pyridine 1.04 g (3.66 mmole) of the compound obtained in step 6 was dissolved in 5 ml of $CH_2Cl_2$ and thereto was added 3.2 g (36.6 mmole) of activated $MnO_2$. The reaction solution was stirred for 16 hours at room temperature and filtered through Cellite. The resultant was concentrated under reduced pressure to obtain 0.57 g of the title compound (yield 55%).

Step 8: Preparation of 6-bromo-2-butyl-5-dimethoxymethyl-1 H-imidazo[4,5-b]pyridine 0.57 g (2.02 mmole) of the compound obtained in step 7 was dissolved in 5 ml of 3% HCl/MeOH and heated to reflux for 30 minutes. The reaction solution was cooled and thereto was added saturated $NaHCO_3$ solution. The resultant was extracted with ethyl acetate. The organic layer was dried over $Na_2SO_4$, concentrated under reduced pressure and purified with column chromatography (hexane:ethyl acetate=1:1) to obtain 0.61 g of the title compound (yield 92%).

Step 9: Preparation of 6-bromo-2-butyl-5-dimethoxymethyl-3-{2'-[1-(1-ethoxyethyl)-1H-tetrazol-5-yl]-biphenyl-4-ylmethyl}-3H-imidazo[4,5-b]pyridine 0.61 g (1.86 mmole) of the compound obtained in step 8 was dissolved in 3 ml of DMF and thereto were added 0.79 g (2.05 mmole) of 2'-[1-(1-ethoxyethyl)-1H-tetrazol-5-yl]-biphenyl-4-ylmethylbromide and 0.51 g (3.72 mmole) of $K_2CO_3$. The resulting solution was stirred at room temperature for 5 hours and diluted with 50 ml of ethyl acetate. The resultant was washed with water (25 ml×3) and dried over $Na_2SO_4$, and then concentrated under reduced pressure and purified with column chromatography (hexane:ethyl acetate=1:1) to obtain 0.7 g of the title compound (yield 59%).

Step 10: Preparation of 2-butyl-5-dimethoxymethyl-6-pyridin-2-yl-3-{2'-[1-(1-ethoxyethyl)-1H-tetrazol-5-yl]-biphenyl-4-ylmethyl}-3H-imidazo[4,5-b]pyridine 0.7 g (1.1 mmole) of the compound obtained in step 9 was dissolved in 5 ml of toluene and to the resulting solution were added 486 mg (1.32 mmole) of 2-(tributyltin)-pyridine and 25 mg (0.022 mmole) of $Pd(PPh_3)_4$. The resultant was heated to reflux for 16 hours under argon gas, cooled and extracted with a mixture of ethyl acetate and water. The organic layer was dried over $MgSO_4$ and concentrated under reduced pressure. The residue was purified with column chromatography (ethyl acetate) to obtain 389 mg of the title compound (yield 56%).

Step 11: Preparation of 2-butyl-5-dimethoxymethyl-6-(1-oxy-pyridin-2-yl)-3-{2'-[1-(1-ethoxyethyl)-1H-tetrazol-5-yl]-biphenyl-4-ylmethyl}-3H-imidazo[4,5-b]pyridine 100 mg (0.16 mmole) of the compound obtained in step 10 was dissolved in 2 ml of $CH_2Cl_2$ and to the resulting solution was added 33 mg (0.19 mmole) of 3-chloroperoxybenzoic acid. The resultant was stirred for 16 hours at room temperature and concentrated under reduced pressure. The residue was purified with column chromatography (5% methanol/dichloromethane) to obtain 68 mg of the title compound (yield 66%).

Step 12: Preparation of 2-butyl-5-formyl-6-(1-oxy-pyridin-2-yl)-3-[2'-(1H-tetrazol-5-yl)-biphenyl-4-ylmethyl]-3H-imidazo[4,5-b]pyridine 100 mg (0.15 mmole) of the compound obtained in step 11 was dissolved in 3 ml of THF and to the resulting solution was added 2 ml of 3N HCl. The resultant was stirred for 1 hour at room temperature and extracted with a mixture of saturated $NaHCO_3$ solution and ethyl acetate. The organic layer was dried over $MgSO_4$ and evaporated under reduced pressure to obtain 64 mg of the title compound (yield 81%).

Step 13: Preparation of 2-butyl-5-hydroxymethyl-6-(1-oxy-pyridin-2-yl)-3-[2'-(1H-tetrazol-5-yl)-biphenyl-4-ylmethyl]-3H-imidazo[4,5-b]pyridine 64 mg (0.12 mmole) of the compound obtained in step 12 was dissolved in 2 ml of methanol and to the resulting solution was added 13 mg (0.36 mmole) of $NaBH_4$. The resultant was stirred for 5 minutes at room temperature and extracted with a mixture of water and ethyl acetate. The organic layer was dried over $MgSO_4$ and evaporated under reduced pressure to remove residual solvent. The residue was purified with column chromatography (20% methanol/dichloromethane) to obtain 51 mg of the title compound (yield 80%).

$^1$H NMR (300 MHz, $CD_3OD$) δ 0.9 (t, 3H), 1.4 (m, 2H), 1.7 (m, 2H), 2.9 (t, 3H), 4.65 (s, 2H), 5.62 (s, 2H), 7.1 (s, 4H), 7.5 (m, 5H), 7.7 (d, 2H), 7.95 (s, 1H), 8.5 (d, 1H)

EXAMPLE 2

Preparation of 2-Butyl-5-hyroxymethyl-6-(1-oxy-pyridin-4-yl)-3-[2'-(1H-tetrazol-5-yl)-biphenyl-4-ylmethyl]-3H-imidazo[4,5-b]pyridine Step 1: Preparation of 2-butyl-5-hyroxymethy1-6-(1-oxy-pyridin-4-yl)-3-{2'-[1-(1-ethoxyethyl)-1H-tetrazol-5-yl]-biphenyl-4-ylmethyl}-3H-imidazo[4,5-b]pyridine.

The same procedures as in steps 10 and 11 of Example 1 were repeated using 100 mg (0.16 mmole) of the compound obtained in step 9 of Example 1 and 71 mg (0.19 mmole) of 4-tributyltin pyridine to obtain 51 mg (0.08 mmole) of the title compound.

Step 2: Preparation of 2-butyl-5-hyroxymethyl-6-(1-oxy-pyridin-4-yl)-3-[2'-(1H-tetrazol-5-yl)-biphenyl-4-ylmethyl]-3H-imidazo[4,5-b]pyridine.

51 mg of the compound obtained in step 1 was dissolved in 3 ml of 1% HCl/MeOH (anhydrous) and the resultant was stirred for 30 minutes at room temperature. To the resulting solution was added saturated aqueous $NaHCO_3$ solution and the resultant was extracted with ethyl acetate. The organic layer was dried over $MgSO_4$ and concentrated under reduced pressure. The residue was purified with column chromatography (20% methanol/dichloromethane) to obtain 27 mg of the title compound (yield 64%).

$^1$H NMR (300 MHz, $CDCl_3+CD_3OD$) δ 0.9 (t, 3H), 1.4 (m, 2H), 1.75 (m, 2H), 2.85 (t, 2H), 4.67 (s, 2H), 5.6 (s, 2H), 7.1 (m, 4H), 7.5 (m, 7H), 8.35 (d, 2H)

EXAMPLE 3

Preparation of 2-Butyl-5-methyl-6-(1-oxy-pyridin-2-yl)-3-[2'-(1H-tetrazol-5-yl)-biphenyl-4-ylmethyl]-3H-imidazo[4,5-b]pyridine The same procedures as in steps 9 to 11 of Example 1 and step 2 of Example 2 were repeated using 210 mg (0.78 mmole) of the compound obtained in step 4 of Example 1 to obtain 145 mg of the title compound (yield 36%).

$^1$H NMR (200 MHz, $CD_3OD$) δ 0.9 (t, 3H), 1.4 (m, 2H), 1.7 (m, 2H), 2.45 (s, 3H), 2.85 (t, 2H), 5.55 (s, 2H), 7.05 (s, 4H), 7.6 (m, 8H), 8.45 (d, 1H)

EXAMPLE 4

Preparation of 2-Butyl-5-methoxycarbonyl-6-(1-oxy-pyridin-2-yl)-3-[2'-(1H-tetrazol-5-yl)-biphenyl-4-ylmethyl]-3H-imidazo[4,5-b]pyridine Step 1: Preparation of 6-bromo-2-butyl-5-methoxycarbonyl-3H-imidazo[4,5-b]pyridine 0.69 g (2.45 mmole) of the compound obtained in step 7 of Example 1 was dissolved in 10 ml of MeOH—$H_2O$ (9:1) and to the resulting solution was added 4.12 g (49 mmole) of $NaHCO_3$. The resultant was stirred until $NaHCO_3$ was dissolved and thereto was added 2.0 ml (4.9 mmole) of $Br_2$. The resulting solution was stirred for 1 hour at room temperature and extracted with a mixture of water and ethyl acetate. The organic layer was dried over $MgSO_4$ and evaporated under reduced pressure to obtain 0.75 g of the title compound (quantitative).

Step 2: Preparation of 2-butyl-5-methoxycarbonyl-6-(1-oxy-pyridin-2-yl)-3-[2'-(1H-tetrazol-5-yl)-biphenyl-4-ylmethyl]-3H-imidazo[4,5-b]pyridine The same procedures as in steps 9 to 11 of Example 1 and step 2 of Example 2 were repeated using 0.75 g (24 mmole) of the compound obtained in step 1 to obtain 323 mg of the title compound (yield 24%).

$^1$H NMR (200 MHz, $CDCl_3+CD_3OD$) δ 0.9 (t, 3H), 1.4 (m, 2H), 1.8 (m, 2H), 2.9 (t, 2H), 3.85 (s, 3H), 5.6 (s, 2H), 7.15 (s, 4H), 7.5 (m, 7H), 8.0 (s, 1H), 8.3 (d, 1H)

EXAMPLE 5

Preparation of 2-Butyl-6-(1-oxy-pyridin-2-yl)-3-[2'-(1H-tetrazol-5-yl)-biphenyl-4-ylmethyl]-3H-imidazo[4,5-b]pyridin-5-carboxylate Diethylamide Step 1: Preparation of 2-butyl-6-pyridin-2-yl-3-{2'-[1-(1-ethoxyethyl)-1H-tetrazol-5-yl]-biphenyl-4-ylmethyl}-3H-imidazo[4,5-b]pyridin-5-carboxylic acid 100 mg (0.16 mmole) of the compound obtained in step 1 of Example 4 was dissolved in 2 ml of MeOH and to the resulting solution was added 2 ml of 1N NaOH. The resultant was stirred for 10 hours at room temperature and neutralized to pH 5 with 1N HCl. The resultant was extracted with ethyl acetate. The organic layer was dried over $MgSO_4$ and evaporated under reduced pressure to obtain 80 mg of the title compound (yield 83%).

Step 2: Preparation of 2-butyl-6-pyridin-2-yl-3-{2'-[1-(1-ethoxyethyl)-1H-tetrazol-5-yl]-biphenyl-4-ylmethyl}-3H-imidazo[4,5-b]pyridin-5-carboxylate diethylamide.

80 mg (0.13 mmole) of the compound obtained in step 1 was dissolved in 2 ml of $CH_2Cl_2$ and to the resulting solution were added 12 mg (0.16 mmole) of diethylamine, 33 mg (0.16 mmole) of DDC(Dithiocarb Sodium) and 2 mg (0.016 mmole) of DMAP. The resultant was stirred for 16 hours at room temperature and evaporated under reduced pressure to remove the residual solvent. The residue was purified with column chromatography (ethyl acetate) to obtain 34 mg of the title compound (yield 40%).

Step 3: Preparation of 2-butyl-6-(1-oxy-pyridin-2-yl)-3-[2'-(1H-tetrazol-5-yl)-biphenyl-4-ylmethyl]-3H-imidazo[4,5-b]pyridine-5-carboxylate diethylamide.

The same procedures as in step 11 of Example 1 and step 2 of Example 2 were repeated using 34 mg (0.05 mmole) of the compound obtained in step 2 to obtain 14 mg of the title compound (yield 48%).

$^1$H NMR (300 MHz, CDCl$_3$+CD$_3$OD) δ 0.9 (m, 6H), 1.15 (m, 6H), 1.4 (m, 2H), 1.75 (m, 2H), 2.9 (t, 2H), 3.2 (m, 2H), 3.3 (m, 2H), 5.45 (s, 2H), 6.9 (d, 2H), 7.0 (d, 2H), 7.4 (m, 7H), 8.0 (s, 1H), 8.35 (d, 1H)

EXAMPLE 6

Preparation of 2-Butyl-5-methyl-6-(1-oxy-pyridin-3-yl)-3-[2'-(1H-tetrazol-5-yl)-biphenyl-4-ylmethyl]-3H-imidazo[4,5-b]pyridine Step 1: Preparation of 6-bromo-2-butyl-5-methyl-3-{2'-[1-(1-ethoxyethyl)-1H-tetrazol-5-yl]-biphenyl-4-ylmethyl}-3H-imidazo[4,5-b]pyridine.

The same procedure as in step 9 of Example 1 was repeated using 250 mg (0.93 mmole) of the compound obtained in step 4 of Example 1 to obtain 290 mg of the title compound (yield 54%).

Step 2: Preparation of 2-butyl-5-methyl-6-(pyridin-3-yl)-3-{2'-[(1-ethoxyethyl)-1H-tetrazol-5-yl]-biphenyl-4-ylmethyl}-3H-imidazo[4,5-b]pyridine.

The same procedure as in step 10 of Example 1 was repeated using 290 mg (0.50 mmole) of the compound obtained in step 1 and 370 mg (1.00 mmole) of 3-(tributyltin)-pyridine to obtain 90 mg of the title compound (yield 32%).

Step 3: Preparation of 2-butyl-5-methyl-6-(1-oxy-pyridin-3-yl)-3-[2'-(1H-tetrazol-5-yl)-biphenyl-4-ylmethyl]-3H-imidazo[4,5-b]pyridine.

The same procedures as in step 11 of Example 1 and step 2 of Example 2 were repeated using 90 mg (0.16 mmole) of the compound obtained in step 2 to obtain 66 mg of the title compound (yield 81%).

$^1$H NMR (CD$_3$OD) δ 0.85 (t, 3H), 1.32 (m, 2H), 1.68 (m, 2H), 2.52 (s, 3H), 2.80 (t, 2H), 5.53 (s, 2H), 7.03 (s, 4H), 7.30~8.00 (m, 7H), 8.38 (m, 2H)

EXAMPLE 7

Preparation of 2-Butyl-5-methyl-6-(1-oxy-pyridin-4-yl)-3-[2'-(1H-tetrazol-5-yl)-biphenyl-4-ylmethyl]-3H-imidazo[4,5-b]pyridine The same procedures as in steps 10 and 11 of Example 1 and step 2 of Example 2 were repeated using 200 mg (0.35 mmole) of the compound obtained in step 1 of Example 6 and 193 mg (0.53 mmole) of 4-(tributyltin)-pyridine to obtain 130 mg of the title compound (yield 71%).

$^1$H NMR (CD$_3$OD) δ 0.88 (t, 3H), 1.30 (m, 2H), 1.66 (m, 2H), 2.57 (s, 3H), 2.81 (t, 2H), 5.53 (s, 2H), 7.05 (s, 4H), 7.40~7.90 (m, 7H), 8.35 (d, 2H)

Activity Test

The inventive compounds were tested to measure their angiotensin II receptor binding capacity, lowering effect of blood pressure in renal hypertension and sustainability as follows. Losartan(Dup 753) and 5,7-dimethyl-2-ethyl-3-[2'-tetrazol-5-yl)-biphen-4-yl]methyl-3H-imidazo[4,5-b]pyridine (referred to as the "Merck compound" throughout this specification), which is disclosed in EP No. 400,974 issued to Merck, were used as the control compounds.

1. Angiotensin II receptor binding assay

In accordance with the procedure disclosed in Chiu, A. T. et al., *Eur. J. Pharm.*, 157, 13(1981), a ligand marked with a radioisotope was reacted with an angiotensin II receptor and the reactant was filtered with a glass fiber to remove unreacted ligand. After washing the filter, the amount of the remaining isotope was measured to determine the binding activity of the ligand, as described below in detail.

(i) Isolation of angiotensin II receptor

Sprague-Dawley rats and Wistar rats of 250 to 350 g (from The Korea Research Institute of Chemical Technology) were tested and the test procedures were carried out at 4° C., unless otherwise specified. Adrenal gland was separated from the Sprague-Dawley rats (liver, in the case of Wistar rats) into cortex and medulla. The separated adrenal cortex and medulla were washed with a sucrose buffer solution (0.2M sucrose, 1 mM EDTA, 10 mM Tris, Ph 7.2) and homogenized in the same buffer solution by using a Teflon pestle and a Brinkmann homogenizer. The homogenates were centrifuged at 3,000× g for 10 minutes to remove precipitates and further centrifuged at 12,000× g for 13 minutes. The final supernatants were centrifuged at 102,000× g for 1 hour to obtain precipitates, which were washed with a Tris buffer solution (50 mM Tris, 5 mM MgCl$_2$, pH 7.2) and recentrifuged at 102,000× g for 1 hour. The resulting precipitates were immediately processed at the following step or stored at −70° C.

The precipitates were suspended in a Tris buffer solution. The amount of protein was determined by using a Bio-Rad DC protein analyzing kit and the protein concentration was adjusted to the amounts of: 0.2 to 0.3 mg/ml (Sprague-Dawley rat: adrenal cortex), 1.5 to 2.0 mg/ml (Sprague-Dawley rat: adrenal medulla), and 1.5 to 2.0 mg/ml (Wistar rat: liver). To the suspension, bovine serum albumin(BSA) was added to a concentration of 0.25 wt % and the resultant was immediately processed at the following step or stored at −70° C.

(ii) Measurement of angiotensin II receptor binding capacity

50 μl (based on ligand) of [$^3$H] angiotensin II (NEN, NET-446) and 10 μl of each of the test compounds with various concentrations were added to the buffer solution (50 mM Tris (pH 7.2), 5 mM MgCl$_2$, 0.25% BSA) to adjust the final volume to be 0.5 ml. 100 μl of the receptor suspension was added thereto and the resulting solution was reacted for 60 minutes while stirring in a water bath at 25° C. 3 ml of cold buffer solution for analysis was added to cease the reaction. The isotope which was bound to the receptor was isolated from the resultant by using Brandel Cell Harvester System with Whatman glass fiber GF/C. After washing the filter, the radioactivity of the filter was determined by using a liquid scintillation counter. Binding inhibition(%) of the test compound was calculated as follows:

$$\text{Binding Inhibition}(\%)=[\{(T-B)-(S-B)\}/(T-B)]\times 100$$

wherein T is the radioactivity (cpm) of the reaction product untreated with the test compound, S is the radioactivity (cpm) of the reaction product treated with the test compound, and B is the radioactivity (cpm) of blank test.

The results are given in Table 1.

2. Blood pressure lowering effect in renal hypertension (i) Induction of renal hypertension To induce renal hypertension, left renal artery of 4 week-old male Sprague-Dawley rat (from The Korea Research Institute of Chemical Technology) was ligated. The rat was anesthetized with ether and the surgical region on the left abdomen of the rat was shaved, disinfected, and then incised about 1 cm vertically. The renal artery near abdominal aorta was isolated carefully from surrounding tissues and veins, and then ligated completely with a suture (4/0 sterile surgical silk). The muscular strata and skin of the surgical area were sutured with a suture (4/0 sterile surgical silk). The surgical region was disinfected to prevent infection and thereafter, 200 to 250 mg/kg/day of cephazolin sodium was injected intramuscularly for 2 days. 6 to 8 days after the ligation, rats showing systolic pressure of more than 180 mmHg were selected for renal hypertension test. The blood pressure was determined by a tail-cuff method from the tail under unanesthetized condition (Gerold, M. et al., *Arzneimittel-Forsch.*, 18, 1285(1968)).

(ii) Blood pressure lowering effect of the compounds

Each of the compounds to be tested was administered intravenously or orally into the renal hypertensive rat. The blood pressure of the rat was determined by direct method (Chiu, A. T. et al., *J. Pharmacol. Exp. Ther.*, 250, 867(1989)) using a catheter. The rat was anesthetized with ketamine hydrochloride (125 mg/kg, i.p.) and a catheter was filled with saline and inserted into a carotid artery and carotid vein. The surgical area was sutured with a metal clip. The rat was relaxed at least 3 hours and the catheter in the carotid artery was adapted to an isotec pressure transducer to determine the blood pressure and heart rate with a physiograph (Linearcorder WR3310). After the blood pressure was stabilized, the test compound was administered intravenously or orally. For intravenous administration, the administered volume and washing volume were 1.0 ml/kg and 0.2 ml, respectively. The blood pressure and heart rate were measured in regular intervals up to 24 hours after the administration of the test compound and compared with those measured after the administration of the control compound Losartan.

The test compound was dissolved in 0.05N KOH for intravenous administration and suspended in Tween 80 for oral administration. The results are given in Table 1.

TABLE 1

| Compound | Binding Inhibition (%) | Maximum Blood Pressure Lowering Effect (Amount) |
|---|---|---|
| Ex. 1 | 85.4 | −60% (3 mg) |
| Ex. 2 | 96.9 | |
| Ex. 3 | 86.4 | −50% (3 mg) |
| Ex. 4 | 92.1 | |
| EX. 5 | 60.3 | |
| Ex. 6 | 94.6 | −38% (3 mg) |
| Ex. 7 | 95.5 | |
| Control Compound (Dup 753) | 48.0 | −27% (10 mg) |

As can be seen from Table 1, the compounds prepared in Examples 1 to 7 have superior effects in a low concentration of 3 mg, compared with that of the control compound in 10 mg.

(iii) Blood pressure lowering effect with respect to dose

The present compounds, Losartan(Dup 753) and the Merck compound were administrated orally to rats in 10, 3 and 1 mg/kg under the same condition as in (ii) and the blood pressure lowering effect was determined. The results are given in Table 2.

TABLE 2

Maximum Blood Pressure Lowering Effect (%)

| Compound | Amount (mg/kg) | | |
|---|---|---|---|
| | 10 | 3 | 1 |
| Losartan (Dup 753) | −46 | −30 | |
| Merck Compound | | −40 | |
| Example 1 | | −(40–60) | −(10–22) |
| Example 3 | | −(40–49) | −20 |
| Example 6 | | −(30–38) | −(13–15) |

As can be seen from Table 2, the present compounds tested above have blood pressure lowering effects superior to that of Losartan(Dup 753) and at least equal to that of the Merck compound.

3. Blood pressure lowering effect in unanesthetized dogs (i) Blood pressure variation with time A number of dog was fed freely in a feeding room and those weighing 7 to 12 kg in good health were selected regardless of their gender.

The test dog was anesthetized with 30 mg/kg of pentobarbital sodium by intravenous injection and the left femoral artery and femoral vein were separated carefully. Silicone catheter, specially prepared and filled with saline treated with heparin (1,000 IU/ml), was cannulated into the blood vessels. After the surgery, the dog was constrained to measure the blood pressure continuously with Gould 2000 physiograph adapted to a Grass P23XL pressure transducer; and the heart rate was monitored with ECG/Biotacho amplifier. The dog was tested at least 2 days after the surgery.

10 mg/kg of furosemide was injected intramuscularly 18 hours (in case of intravenous injection, 2 hours) before the beginning of the test (administration of the test compound) to improve the activity of renin in blood plasma. After the injection of furosemide, neither food nor water was provided. The test compound was suspended in Tween 80 and administered in an amount of 20 mg/kg orally. The blood pressure and heart rate were measured up to 8 hours after the administration of each test compound. The results are given in Table 3.

TABLE 3

Maximum Blood Pressure Lowering Effect (%)

| Compound | Time (hr) | | | | | |
|---|---|---|---|---|---|---|
| | 0.5 | 1 | 2 | 4 | 6 | 8 |
| Ex. 1 (1.0 mg) | −17.5 | −21.4 | −23.6 | −24.8 | −21.7 | −13.2 |
| Ex. 3 (1.0 mg) | −16.2 | −23.8 | −30.0 | −32.7 | −35.5 | −33.0 |
| Control (Dup 753) (3 mg) | −11.0 | −12.3 | −12.8 | −9.9 | −10.1 | −8.2 |

As can be seen from Table 3, the maximum blood pressure lowering effect of the present compounds lasted up to 8 hours after the administration, while that of the control compound lasted up to 2 hours and decreased thereafter.

(ii) Maximum blood pressure lowering effect

The maximum blood pressure lowering effect of the present compounds and the control compounds were determined in different amounts of administration using the same method as (i) and the results are given in Table 4.

TABLE 4

Maximum Blood Pressure Lowering Effect (%)

| Compound | Amount (mg/kg) | | | | |
|---|---|---|---|---|---|
| | 10 | 3 | 1 | 0.3 | 0.1 |
| Losartan (Dup 753) | −23 | −13 | | | |
| Merck Compound | | | | −24 | −20 |
| Example 1 | | | −25 | −17 | |
| Example 3 | | | −37 | −11 | −10 |
| Example 6 | | | −12 | −9 | |

4. Duration of action (i) Duration of action in renal hypertensive rats

The compound of Example 1 and the Merck compound were tested using the hypertensive rats of test 2(i). 3 mg/kg of each compound was administered orally and blood pressure lowering effect with time was determined to measure the duration of action of the compounds. The results are given in Table 5.

TABLE 5

Maximum Blood Pressure Lowering Effect (%)

| Time (min.) | Example 1 (3 mg/kg) | Merck Compound (3 mg/kg) |
|---|---|---|
| 0 | 0 | 0 |
| 10 | −11 | −15 |
| 20 | −19 | −27 |
| 30 | −32 | −28 |
| 60 | −48 | −26 |
| 90 | −42 | −28 |
| 120 | −44 | −25 |
| 240 | −58 | −40 |
| 360 | −60 | −36 |
| 1320 | −48 | −35 |
| 1440 | −49 | −40 |

As can be seen from Table 5, the blood pressure lowered by the compound of Example 1 showed −60% at 360 minutes after the administration, while that of the Merck compound showed −40% at 240 minutes after the administration, which proves that the present compound has a far longer duration of action than the Merck compound.

(ii) Duration of action in furosemide-administered dogs

The compound of Example 1 and the Merck compound were administered orally to the furosemide-administrated dogs as in test 3(i), and blood pressure lowering effect was measured with time. The results are given in Table 6.

TABLE 6

Maximum Blood Pressure Lowering Effect (%)

| Time (min.) | Example 1 (0.3 mg) | Merck Compound (0.3 mg) |
|---|---|---|
| 0 | 0.0 | 0.0 |
| 10 | 2.2 | −5.0 |
| 20 | −1.1 | −12.2 |
| 30 | −5.9 | −14.4 |
| 60 | −11.4 | −20.1 |
| 90 | −12.9 | −24.4 |
| 120 | −14.8 | −19.1 |
| 150 | −16.1 | −24.2 |
| 180 | −16.7 | −18.9 |
| 210 | −17.4 | −17.0 |
| 240 | −18.2 | −17.0 |

TABLE 6-continued

Maximum Blood Pressure Lowering Effect (%)

| Time (min.) | Example 1 (0.3 mg) | Merck Compound (0.3 mg) |
|---|---|---|
| 270 | −17.0 | −13.4 |
| 300 | −20.5 | −14.9 |
| 330 | −20.7 | −15.6 |
| 360 | −20.4 | −15.6 |
| 390 | −20.1 | −11.4 |
| 420 | −20.5 | −10.7 |
| 450 | −20.5 | −11.4 |
| 480 | −20.0 | −13.8 |

As can be seen from Table 6, the maximum blood pressure lowering effect of the compound of Example 1 lasted up to 8 hours after the administration, while that of the Merck compound lasted up to 2 to 3 hours and decreased thereafter.

5. Metabolite analysis

Enzyme digestion test was executed in order to detect the metabolite of the test compound in vivo.

500 μg of NADP$^+$, 11 U of glucose-6-phosphate dehydrogenase and 200 μg of rat liver microsome were added to 1 ml of 0.1M phosphate buffer (pH 7.4), and to the resulting solution was added glucose-6-phosphate to a concentration of 10 mM. The resultant was incubated for 1 minute at 37° C. and added with each of the present compound (Example 3) and the Merck compound to a concentration of 100 μM. The mixture was incubated for 1 hour at 37° C., and then was added with 2 ml of dichloromethan to cease the reaction. The resultant was extracted with dichloromethan and the extract was evaporated to obtain a residue. The reside was analyzed using HPLC after dissolving in a mobile phase of the HPLC.

Condition for HPLC

Column: Nucleosil phenyl column (0.46×25 cm, 5 μM)

Mobile phase: acetonitrile (50 mM, pH 5.0; 35:65, v/v)

Flow rate: 1.0 ml/min.

Detector: UV 250 nm

FIG. 1 is a HPLC chart showing the result of the enzyme digestion test of the Merck compound and the compound of Example 3.

Figure 1B:
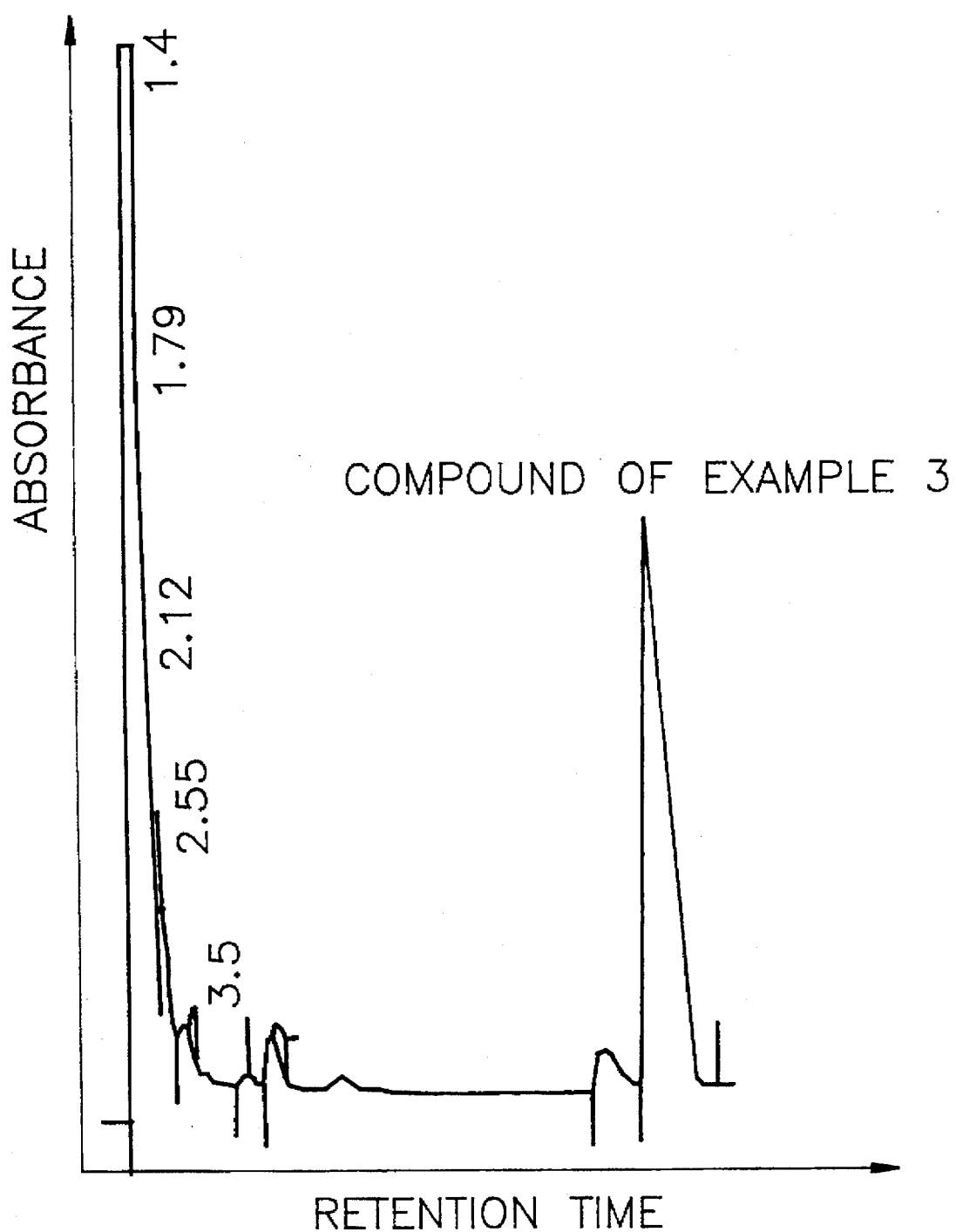

As can be seen from FIG. 1A, the Merck compound has a metabolite, which corresponds to a peak at 10 minutes of retention time, resulting from an enzymatic digestion. In contrast, as shown in FIG. 1B, the compound of Example 3 has no metabolite from the enzymatic digestion. Such result proves that the present compound has a good stability against the enzymatic digestion, in contrast with the Merck compound.

While the invention has been described with respect to the specific embodiments contained herein, it should be recognized that various modifications and changes which may be apparent to those skilled in the art to which the invention pertains may be made and also fall within the scope of the invention as defined in the claims that follow.

What is claimed is:

1. A pyridyl imidazole compound, and pharmacologically acceptable salts thereof, of formula(I):

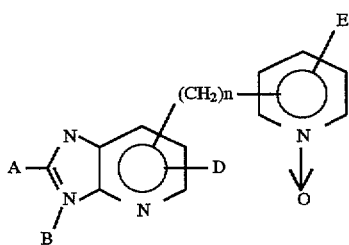

(I)

wherein:

A is a straight, branched or cyclic $C_1$–$C_6$ alkyl or alkenyl group, $OR^1$ (wherein $R^1$ is a hydrogen, or a straight, branched or cyclic $C_1$–$C_6$ alkyl or alkenyl radical), or $NR^2R^3$ (wherein $R^2$ and $R^3$ are independently a hydrogen, or a straight, branched or cyclic $C_1$–$C_6$ alkyl radical);

B is a group of the following formula

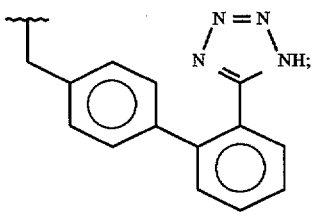

D is a hydrogen; a halogen; a straight, branched or cyclic $C_1$–$C_6$ alkyl, $C_2$–$C_6$ alkenyl or $C_2$–$C_6$ alkynyl group which is optionally substituted with OH, a $C_1$–$C_4$ alkoxy radical, $CO_2R^1$, $COR^1$, $CON(R^1)_2$ or $N(R^1)_2$, wherein $R^1$ is the same as defined above; tetrazol-5-yl; a perfluoro-$C_1$–$C_4$ alkyl group; or $N(R^1)_2$, $OR^1$, $CO_2R^1$ or $CON(R^1)_2$, wherein $R^1$ is the same as defined above;

E is a hydrogen; a halogen; a straight or branched $C_1$–$C_6$ alkyl, $C_2$–$C_6$ alkenyl or $C_2$–$C_6$ alkynyl group which is optionally substituted with OH, a $C_1$–$C_4$ alkoxy radical, $CO_2R^1$, $COR^1$, $CON(R^1)_2$ or $N(R^1)_2$, wherein $R^1$ is the same as defined above; a perfluoro-$C_1$–$C_4$ alkyl group; $NO_2$; or $N(R^1)_2$ or $OR^1$; wherein $R^1$ is the same as defined above; and n is 0 or an integer of 1 to 4.

2. The compound of claim 1, wherein

A is a straight, branched or cyclic $C_2$–$C_6$ alkyl group or $OR^1$ (wherein $R^1$ is a straight, branched or cyclic $C_2$–$C_5$ alkyl radical);

B is a group of the following formula

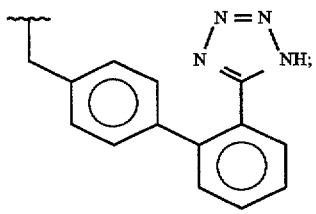

D is a hydrogen, a straight, branched or cyclic $C_1$–$C_4$ alkyl or alkenyl group which is optionally substituted with OH, a $C_1$–$C_2$ alkoxy radical, $CO_2R^1$, $COR^1$ or $N(R^1)_2$, wherein $R^1$ is the same as defined above;

E is a hydrogen, or a straight, branched or cyclic $C_1$–$C_4$ alkyl or alkenyl group; and n is 0, 1 or 2.

3. The compound of claim 1 which is selected from the group consisting of:

2-butyl-5-methyl-6-(1-oxy-pyridin-2-yl)-3-[2'-(1H-tetrazol-5-yl)-biphenyl-4-ylmethyl]-3H-imidazo[4,5-b]pyridine;

2-butyl-5-methyl-6-(1-oxy-2-methyl-pyridin-6-yl)-3-[2'-(1H-tetrazol-5-yl)-biphenyl-4-ylmethyl]-3H-imidazo[4,5-b]pyridine;

2-butyl-5-methyl-6-(1-oxy-3-methyl-pyridin-6-yl)-3-[2'-(1H-tetrazol-5-yl)-biphenyl-4-ylmethyl]-3H-imidazo[4,5-b]pyridine;

2-butyl-5-methyl-6-(1-oxy-4-methyl-pyridin-6-yl)-3-[2'-(1H-tetrazol-5-yl)-biphenyl-4-ylmethyl]-3H-imidazo[4,5-b]pyridine;

2-butyl-5-methyl-6-(1-oxy-pyridin-3-yl)-3-[2'-(1H-tetrazol-5-yl)-biphenyl-4-ylmethyl]-3H-imidazo[4,5-b]pyridine;

2-butyl-5-methyl-6-(1-oxy-pyridin-4-yl)-3-[2'-(1H-tetrazol-5-yl)-biphenyl-4-ylmethyl]-3H-imidazo[4,5-b]pyridine;

2-butyl-5-methyl-6-(1-oxy-2-methyl-pyridin-3-yl)-3-[2'-(1H-tetrazol-5-yl)-biphenyl-4-ylmethyl]-3H-imidazo[4,5-b]pyridine;

2-butyl-5-methyl-6-(1-oxy-6-methyl-pyridin-3-yl)-3-[2'-(1H-tetrazol-5-yl)-biphenyl-4-ylmethyl]-3H-imidazo[4,5-b]pyridine;

2-butyl-5-hydroxymethyl-6-(1-oxy-pyridin-2-yl)-3-[2'-(1H-tetrazol-5-yl)-biphenyl-4-ylmethyl]-3H-imidazo[4,5-b]pyridine;

2-butyl-5-(2-hydroxyethyl-1-yl)-6-(1-oxy-pyridin-2-yl)3-[2'-(1H-tetrazol-5-yl)-biphenyl-4-ylmethyl]-3H-imidazo[4,5-b]pyridine;

2-butyl-5-methoxycarbonyl-6-(1-oxy-pyridin-2-yl)-3-[2'-(1H-tetrazol-5-yl)-biphenyl-4-ylmethyl]-3H-imidazo[4,5-b]pyridine;

2-butyl-5-(N,N-diethylcarbamoyl)-6-(1-oxy-pyridin-2-yl)-3-[2'-(1H-tetrazol-5-yl)-biphenyl-4-ylmethyl]-3H-imidazo[4,5-b]pyridine;

2-butyl-6-(1-oxy-pyridin-2-yl)-3-[2'-(1H-tetrazol-5-yl)-biphenyl-4-ylmethyl]-3H-imidazo[4,5-b]pyridine;

2-butyl-5-(N,N-dimethylamino)-6-(1-oxy-pyridin-2-yl)-3-[2'-(1H-tetrazol-5-yl)-biphenyl-4-ylmethyl]-3H-imidazo[4,5-b]pyridine;

2-butyl-5-ethyl-6-(1-oxy-pyridin-2-yl)-3-[2'-(1H-tetrazol-5-yl)-biphenyl-4-ylmethyl]-3H-imidazo[4,5-b]pyridine;

2-butyl-5-fluoro-6-(1-oxy-pyridin-2-yl)-3-[2'-(1H-tetrazol-5-yl)-biphenyl-4-ylmethyl]-3H-imidazo[4,5-b]pyridine;

2-butyl-5-methyl-6-(1-oxy-pyridin-2-ylmethyl)-3-[2'-(1H-tetrazol-5-yl)-biphenyl-4-ylmethyl]-3H-imidazo[4,5-b]pyridine;

2-butyl-5-methyl-6-(1-oxy-pyridin-3-ylmethyl)-3-[2'-(1H-tetrazol-5-yl)-biphenyl-4-ylmethyl]-3H-imidazo[4,5-b]pyridine;

2-butyl-5-methyl-6-[2-(1-oxy-pyridin-2-yl)ethyl-1-yl]-3-[2'-(1H-tetrazol-5-yl)-biphenyl-4-ylmethyl]-3H-imidazo[4,5-b]pyridine;

2-butyl-5-methyl-6-[2-(1-oxy-pyridin-3-yl)ethyl-1-yl]-3-[2'-(1H-tetrazol-5-yl)-biphenyl-4-ylmethyl]-3H-imidazo[4,5-b]pyridine;

2-ethyl-5-methyl-6-(1-oxy-pyridin-2-yl)-3-[2'-(1H-tetrazol-5-yl)-biphenyl-4-ylmethyl]-3H-imidazo[4,5-b]pyridine;

2-ethoxy-5-methyl-6-(1-oxy-pyridin-2-yl)-3-[2'-(1H-tetrazol-5-yl)-biphenyl-4-ylmethyl]-3H-imidazo[4,5-b]pyridine;

2-propyl-5-methyl-6-(1-oxy-pyridin-2-yl)-3-[2'-(1H-tetrazol-5-yl)-biphenyl-4-ylmethyl]-3H-imidazo[4,5-b]pyridine;

2-butyl-5-hydroxymethyl-6-(1-oxy-2-methyl-pyridin-6-yl)-3-[2'-(1H-tetrazol-5-yl)-biphenyl-4-ylmethyl]-3H-imidazo[4,5-b]pyridine;

2-butyl-5-hydroxymethyl-6-(1-oxy-pyridin-4-yl)-3-[2'-(1H-tetrazol-5-yl)-biphenyl-4-ylmethyl]-3H-imidazo[4,5-b]pyridine;

2-butyl-5-hyroxymethyl-6-(1-oxy-pyridin-3-yl)-3-[2'-(1H-tetrazol-5-yl)-biphenyl-4-ylmethyl]-3H-imidazo[4,5-b]pyridine; and mixtures thereof.

4. The compound of claim 3 which is selected from the group consisting of:

2-butyl-5-methyl-6-(1-oxy-pyridin-2-yl)-3-[2'-(1H-tetrazol-5-yl)-biphenyl-4-ylmethyl]-3H-imidazo[4,5-b]pyridine;

2-butyl-5-methyl-6-(1-oxy-2-methyl-pyridin-6-yl)-3-[2'-(1H-tetrazol-5-yl)-biphenyl-4-ylmethyl]-3H-imidazo[4,5-b]pyridine;

2-butyl-5-methyl-6-(1-oxy-pyridin-3-yl)-3-[2'-(1H-tetrazol-5 -yl)-biphenyl-4-ylmethyl]-3H-imidazo[4,5-b]pyridine;

2-butyl-5-methyl-6-(1-oxy-pyridin-4-yl)-3-[2'-(1H-tetrazol-5-yl)-biphenyl-4-ylmethyl]-3H-imidazo[4,5-b]pyridine;

2-butyl-5-hydroxymethyl-6-(1-oxy-pyridin-2-yl)-3-[2'-(1H-tetrazol-5-yl)-biphenyl-4-ylmethyl]-3H-imidazo[4,5-b]pyridine;

2-butyl-5-methoxycarbonyl-6-(1-oxy-pyridin-2-yl)-3-[2'-(1H-tetrazol-5-yl)-biphenyl-4-ylmethyl]-3H-imidazo[4,5-b]pyridine;

2-butyl-6-(1-oxy-pyridin-2-yl)-3-[2'-(1H-tetrazol-5-yl)-biphenyl-4-ylmethyl]-3H-imidazo[4,5-b]pyridine;

2-butyl-5-hydroxymethyl-6-(1-oxy-2-methyl-pyridin-6-yl)-3-[2'-(1H-tetrazol-5-yl)-biphenyl-4-ylmethyl]-3H-imidazo[4,5-b]pyridine;

2-butyl-5-hyroxymethyl-6-(1-oxy-pyridin-4-yl)-3-[2'-(1H-tetrazol-5-yl)-biphenyl-4-ylmethyl]-3H-imidazo[4,5-b]pyridine;

2-butyl-5-hyroxymethyl-6-(1-oxy-pyridin-3-yl)-3-[2'-(1H-tetrazol-5-yl)-biphenyl-4-ylmethyl]-3H-imidazo[4,5-b]pyridine; and mixtures thereof.

5. The compound of claim 4 which is selected from the group consisting of:

2-butyl-5-methyl-6-(1-oxy-pyridin-2-yl)-3-[2'-(1H-tetrazol-5-yl)-biphenyl-4-ylmethyl]-3H-imidazo[4,5-b]pyridine;

2-butyl-5-methyl-6-(1-oxy-pyridin-3-yl)-3-[2'-(1H-tetrazol-5-yl)-biphenyl-4-ylmethyl]-3H-imidazo[4,5-b]pyridine;

2-butyl-5-methyl-6-(1-oxy-pyridin-4-yl)-3-[2'-(1H-tetrazol-5-yl)-biphenyl-4-ylmethyl]-3H-imidazo[4,5-b]pyridine;

2-butyl-5-hydroxymethyl-6-(1-oxy-pyridin-2-yl)-3-[2'-(1H-tetrazol- 5-yl)-biphenyl-4-ylmethyl]-3H-imidazo[4,5-b]pyridine;

and mixtures thereof.

6. A process for preparing a compound of formula(I') which comprises:

(A) condensing a compound of formula(II) with a carboxylic acid of formula ACOOH or an ester of formula ACOOR (wherein, A is the same as defined in claim 1 and R is a methyl or ethyl group) to give a compound of formula(III);

(B) reacting the compound of formula(III) with a compound of formula(IV) in the presence of a base to give a compound of formula(V);

(C) reacting the compound of formula(V) with a compound of formula(VI) in the presence of tetrakis(triphenylphosphine) palladium(O) to give a compound of formula(VII); and (D) oxidizing the compound of formula(VII) with an oxidizing agent:

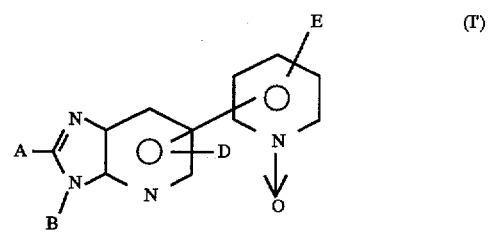 (I')

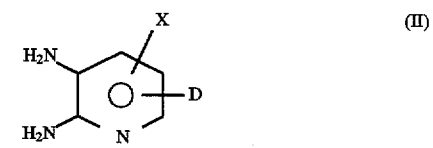 (II)

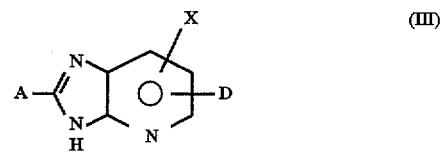 (III)

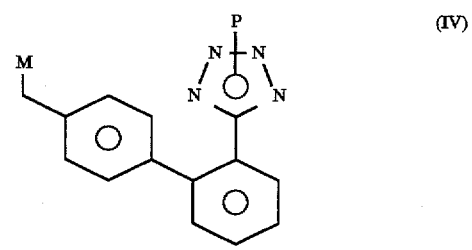 (IV)

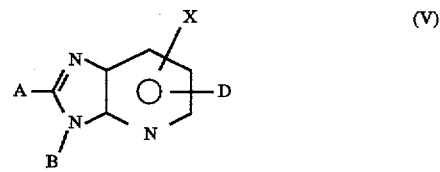 (V)

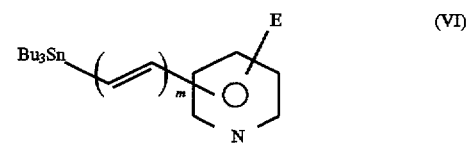 (VI)

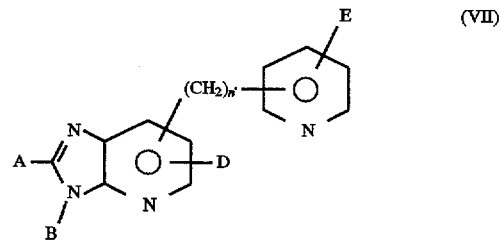 (VII)

wherein:

X is a halogen or trifluoromethanesulfonate;
M is a leaving group;
P is a tetrazole protecting group;
m is 0;
n' is 0; and
A, B, D and E are the same as defined in claim 1.

7. A process for preparing a compound of formula(I'') which comprises:

(A) condensing a compound of formula(II) with a carboxylic acid of formula ACOOH or an ester of formula ACOOR (wherein, A and R are the same as defined in claim 6) to a compound of formula(III);

(B) reacting the compound of formula(III) with a compound of formula(IV) in the presence of a base to give a compound of formula(V);

(C) reacting the compound of formula(V) with a compound of formula(VI) in the presence of tetrakis(triphenylphosphine)palladium(O) to give a compound of formula(VIII);

(D) oxidizing the compound of formula(VIII) with ozone to give a compound of formula(IX);

(E) reacting the compound of formula(IX) with a compound of formula(X) to give a compound of formula (XI);

(F) reacting the compound of formula(XI) with methanesulfonyl chloride to give a compound of formula(XII);

(G) reducing the compound(XII) with tributyltin hydride to give a compound of formula(VII); and (H) oxidizing the compound of formula(VII) with an oxidizing agent:

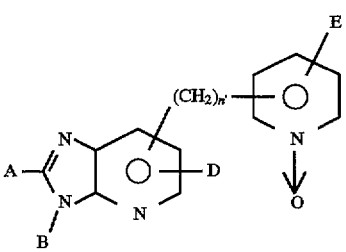
(I''')

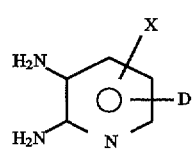
(II)

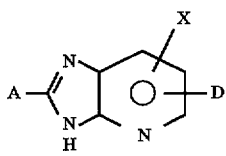
(III)

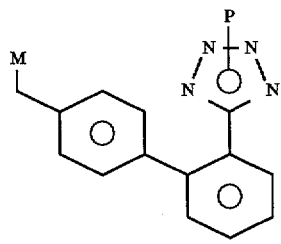
(IV)

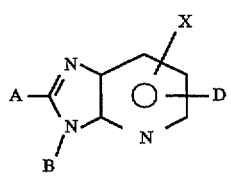
(V)

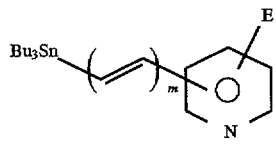
(VI)

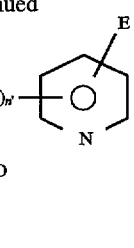
(VII)

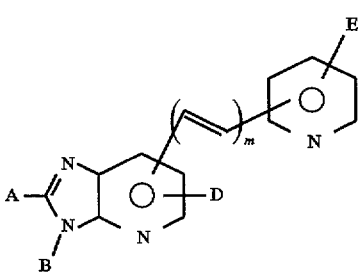
(VIII)

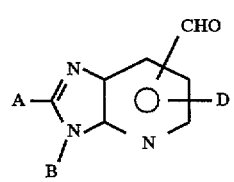
(IX)

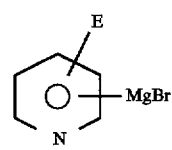
(X)

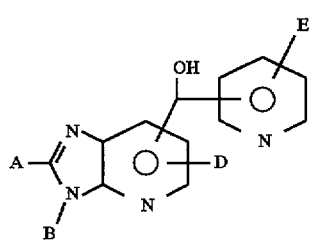
(XI)

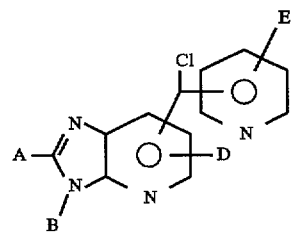
(XII)

wherein:
B, D, E, M, P and X are the same as defined in claim 6;
m is 0 or 1; and
n' is 1.

8. A process for preparing a compound of formula(I''') which comprises:

(A) condensing a compound of formula(II) with a carboxylic acid of formula ACOOH or an ester of formula ACOOR (wherein, A and R are the same as defined in claim 6) to give a compound of formula(III);

(B) reacting the compound of formula(III) with a compound of formula(IV) in the presence of a base to give a compound of formula(V);

(C) reacting the compound of formula(V) with a compound of formula(VI) in the presence of tetrakis (triphenylphosphine) palladium(O) to give a compound of formula(VIII);

(D) hydrogenating the compound of formula(VIII) in the presence of a palladium catalyst to give a compound of formula(VII); and (E) oxidizing the compound of formula(VII) with an oxidizing agent:

wherein:

B, D, E, M, P and X are the same as defined in claim 6;

m is 1; and n' is 2.

9. A pharmaceutical composition comprising a therapeutically effective amount of the pyridyl imidazole compound of claim 1 and a pharmaceutically acceptable carrier.

* * * * *

UNITED STATES PATENT AND TRADEMARK OFFICE
CERTIFICATE OF CORRECTION

PATENT NO. : 5,691,348

DATED : November 25, 1997

INVENTOR(S) : Sung-Eun Yoo, et al

It is certified that error appears in the above-identified patent and that said Letters Patent is hereby corrected as shown below:

ON THE TITLE PAGE:

Item [75] should read --

Young-Ah Shin, Chungcheongbuk, Rep. of Korea

--.

Signed and Sealed this

Fourteenth Day of April, 1998

Attest:

BRUCE LEHMAN

Attesting Officer

Commissioner of Patents and Trademarks